United States Patent [19]

Tomita

[11] Patent Number: 4,797,188

[45] Date of Patent: Jan. 10, 1989

[54] SHEET TYPE ELECTRODE FOR USE IN MEASUREMENT OF IONS

[75] Inventor: Katsuhiko Tomita, Miyanohigashi, Japan

[73] Assignee: Horiba, Ltd., Kyoto, Japan

[21] Appl. No.: 124,909

[22] Filed: Nov. 24, 1987

[30] Foreign Application Priority Data

Mar. 16, 1987 [JP] Japan ................................ 62-61633

[51] Int. Cl.$^4$ .......................................... G01N 27/30
[52] U.S. Cl. .................................. 204/414; 204/416; 204/418; 204/419; 204/420
[58] Field of Search ............... 204/414, 416, 418, 419, 204/420

[56] References Cited

U.S. PATENT DOCUMENTS 4,549,951 10/1985 Knudson et al. .................... 204/416
4,713,165 12/1987 Conover et al. ..................... 204/403

Primary Examiner—G. L. Kaplan
Attorney, Agent, or Firm—Price, Gess & Ubell

[57] ABSTRACT

An improved electrode assembly for measuring ions, such as a pH electrode, and method of forming the same is provided. A plastic support layer with an aperture is mounted over a base member having electrodes. A gelatinized internal solution is mounted in the aperture over the electrodes in a plasticized solution containing a hydrogen ion-responsive material is formed into a paste and is positioned over the gelatinized internal solution and the adjacent surrounding areas of the support layer. When the paste solidifies it forms a thin film plastic ion-selective response membrane that is integrally sealed to the support layer.

9 Claims, 4 Drawing Sheets

SHEET TYPE ELECTRODE FOR USE IN MEASUREMENT OF IONS

BACKGROUND OF THE INVENTION
1. Field of the Invention

The present invention relates to a sheet type electrode for use in the measurement of ions, such as an electrode used in the measurement of an ionic concentration such as pH.
2. Description of the Technical Background Recently, in order to miniaturize a construction of an electrode for measuring an ionic concentration such as pH while reducing the cost of production, and improving its operation and maintenance, there have been attempts to provide the electrode in the form of a sheet.

FIG. 5 shows an external appearance of a sheet type composite electrode for use in the measurement of pH according to a recently filed Japanese Patent Application No. Sho 61-285371 filed by the present Applicant Horiba, Ltd. and FIG. 6 shows a cross section of a measuring electrode of FIG. 5. Referring now to both FIG. 5 and FIG. 6, reference numeral 51 designates a substrate formed of a material, such as a polyethylene terephthalate (hereinafter referred to as PET), having a sufficiently high electrical insulating property even when it is immersed in a solution containing electrolytes. Reference numeral 52 designates an electrode formed on an upper surface of the substrate 51. The electrode 52 can be formed by subjecting the substrate to a preparatory treatment, for example, an appointed surface pretreatment and then a silk screen printing of an Ag paste to form electrode 52. A portion of the electrode 52 is formed as an internal electrode portion 53 coated with an electrode material such as AgCl, and the rest of the electrode 52 is formed as an electrical lead portion 54.

A support layer 55 is formed over a portion of the substrate 51 and is provided with a through hole 56 at a place corresponding to the internal electrode portion 53. The support layer 55 is formed of a material, such as PET, having a sufficiently high electrical insulating property even though it is to be immersed in solutions containing electrolytes. The support layer 55 can be formed on the substrate 51 while still exposing the lead portion 54 and a circumference area around the lead portion 54.

The through hole 56 can be filled with a disc type gelatinized internal solution 57 prepared by adding a gelatinizer, such as agar-agar, and a gel-evaporation inhibitor, such as glycerine, to a basic internal solution obtained by adding a phosphoric acid-buffering agent to a 3.3M-aqueous solution of KCl supersaturated with for example AgCl. The mixture can be heated to turn it into a paste and then placed on the internal electrode portion 53 by a screen printing method and the like, so that an upper surface of the disc type gelatinized internal solution 57 may be slightly projected over an upper surface of the support layer 55.

Reference numeral 58 designates an ion-selective response membrane formed in a thin film-like shape. The ion-selective response membrane 58 is obtained for example by dissolving polyvinyl chloride resin powders in tetrahydrofuran as a solvent, adding tri-n-octylphosphine oxide as a hydrogen ion-responsive substance to the resulting solution together with a plasicizer, while sufficiently stirring the resulting mixture, and evaporating tetrahydrofuran. The ion-selective response membrane 58 is fixedly mounted on the upper surface of the support layer 55 along a circumference of the hole 56 by the use of organic high molecular adhesives 59, such as a polyvinyl chloride resin series adhesive or silicon series adhesive, also having a sufficiently high electrical insulating property. The membrane 58 forms an interface of the measuring electrode with its lower surface adhered to an upper surface of the gelatinized internal solution 57 which is tightly filled on the inside of the through hole 56.

Referring to FIG. 5, reference numeral 60 designates a liquid junction membrane that can be formed of an inorganic sintered porous material, an organic high molecular porous material or the like impregnated with KCl. The liquid junction membrane 60 is also fixedly mounted on the upper surface of the support layer 55 along a circumference thereof so that its lower surface may contact an upper surface of another gelatinized internal solution (not shown) to be formed as a reference electrode. The internal construction of the liquid junction membrane 60 can be almost the same as that of the measuring electrode shown in FIG. 6. Reference numeral 61 designates a casing whose upper surface forms a sample solution holder portion.

With the above described construction, adhesives capable of maintaining a complete seal between the support layer 55 and the response membrane 58 are difficult to obtain. Although polyvinyl chloride resin series organic high molecular adhesives are superior in providing a speedy drying property, they have a disadvantage in that a surface coating is apt to be produced. In addition, silicon series organic high molecular adhesives have problems in providing the stability of adhering conditions such as hardening time and viscosity. In short, the use of any one of these organic high molecular adhesives cannot be expected to provide a complete seal. Accordingly, an electrode having the above described construction has room for improvement in this respect.

SUMMARY OF THE INVENTION

The present invention was achieved in view of the above described matters. It is an object of the present invention to provide a sheet type electrode for use in the measurement of ions capable of forming a response membrane having a complete seal against a support layer and capable of mass production.

In order to achieve the above described object, a sheet type electrode for use in the measurement of ions according to the present invention is characterized by a support layer formed of two sheet materials having a sufficiently high electrical insulating property and a thin film-like ion-selective response membrane formed by positioning on the support layer an ion-selective response membrane paste containing solvents compatible with the support layer.

With the above described construction, a dissolving action occurs between the solvents contained in the ion-selective response membrane paste and the support layer. The solvents are evaporated and the paste is solidified so as to be integrated with the support layer, so that the ion-selective response membrane is formed on the support layer with a complete sealing property.

BRIEF DESCRIPTION OF THE DRAWINGS

One preferred embodiment of the present invention is shown in FIGS. 1 to 3, in which.

DESCRIPTION OF THE PREFERRED EMBODIMENT

The preferred embodiment of the present invention will be described with reference to the drawings. A sheet type composite electrode assembly for use in the measurement of pH is given as an example.

Figure 1:
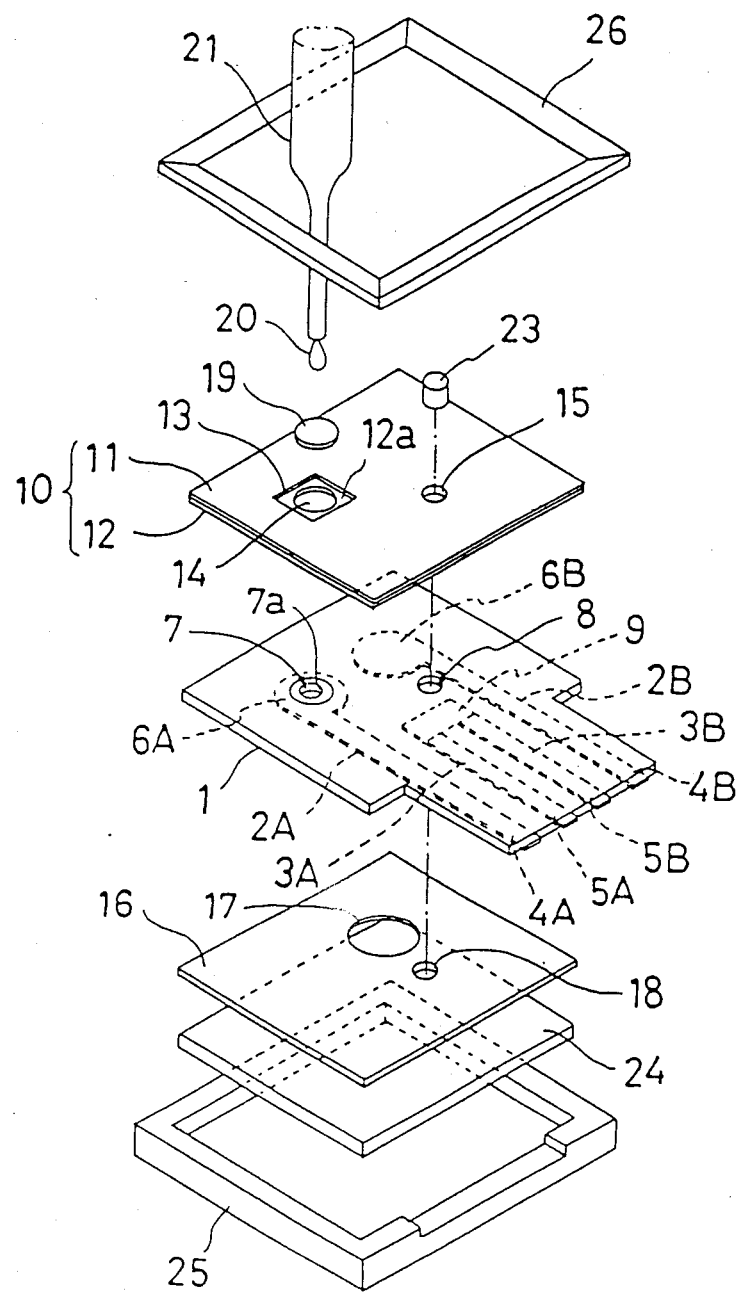
FIG. 1 is an exploded perspective view showing a sheet type composite electrode for use in the measurement of pH according to the present invention.
Figure 2:
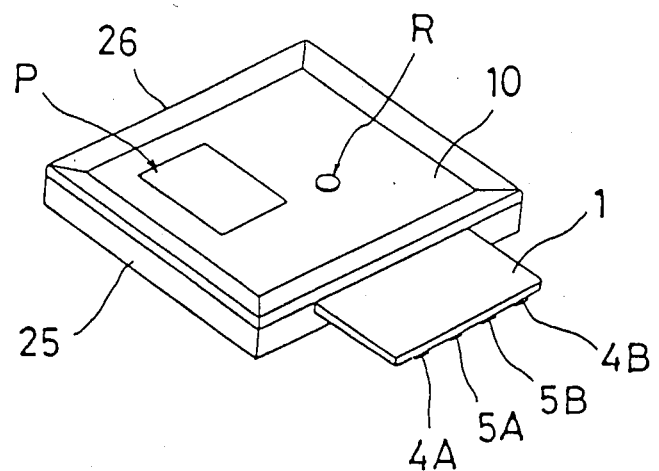
FIG. 2 is a perspective view showing an external appearance of the electrode shown in FIG. 1.
Figure 3:
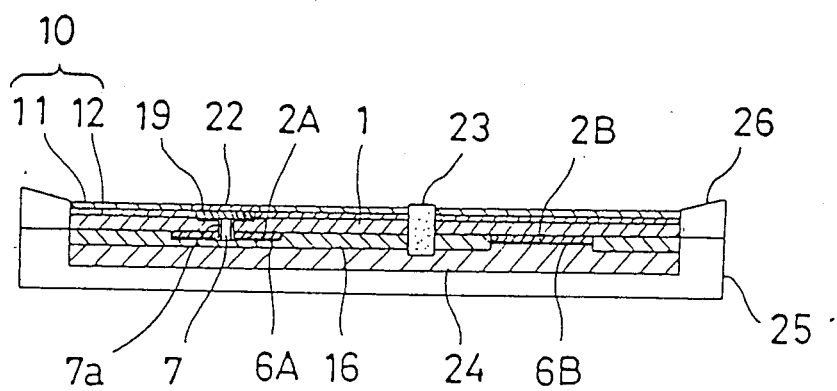
FIG. 3 is a partially developed sectional view of FIG. 2.

Referring now to FIGS. 1 to 3, reference numeral 1 designates a substrate formed of a material, such as polyethylene terephthalate (hereinafter referred to as PET), having a sufficiently high electric insulating property even though it is immersed in a solution containing electrolytes. In addition, the substrate 1 may be formed of organic high molecular materials, such as polyvinyl chloride resin (hereinafter referred to PVC), polyethylene, polypropylene, acryl and polyfluoroethylene, and inorganic materials, such as silica glass and pyrex glass, in addition to PET.

The substrate 1 is provided with two pairs (an inside pair and an outside pair) of electrodes 2A, 2B, and 3A, 3B formed on a lower surface thereof by adhering an electrically conductive metal selected from a group consisting of Ag, Cu, Au, Pt and the like and alloys thereof or a paste containing such a metal or a semiconductor, such as $IrO_2$ and $SnO_2$, to the lower surface thereof by means of physical plating methods, such as a vacuum vapor depositing method and CVD method, chemical plating methods, such as electrolytic method and non-electrolytic method, or printing methods, such as a silk screen method, anastatic printing method and flat plate printing method (in this example the lower surface of the substrate 1 is subjected to a grafting process and an anchoring treatment by the use of a silane coupling agent and the like and then an Ag paste is silk screened on the lower surface of the substrate 1).

A base end portion of each of the electrodes 2A, 2B, 3A, 3B is positioned at one edge portion of the substrate 1 and formed as an electrical lead portion 4A, 4B, 5A, 5B as it is, the other almost circular pointed end portion of the outside pair of electrodes 2A, 2B positioned at an almost central portion of the substrate 1 is formed as internal electrode portions 6A, 6B and they are coated with an electrode material such as AgCl (by means of physical plating methods or chemical plating methods or printing methods in the same manner as above described). One internal electrode portion 6A (pH measuring electrode P side) is provided in its center with an aperture or a through hole 7 (7a designates an electrically conductive portion within the through hole 7) as an electrode through hole subjected to an electrically conductive treatment on an inside surface. Adjacent the other internal electrode portion 6B (reference electrode R side) is a through hole 8 formed in the substrate. In addition, the inside pair of electrodes 3A, 3B are provided with a temperature-compensating electrode portion 9, such as a thermistor, extending between the other pointed end portions positioned at an almost central portion of the substrate 1.

Reference numeral 10 designates a support layer formed of two sheet members 11, 12 having a sufficiently high electrical insulating property piled up by the use of adhesives. For example, the upper sheet member 11 is formed of PET while the lower sheet member 12 is formed of PVC. This support layer 10 is formed for example by subjecting adhering surface sides of both sheet members 11, 12 to a surface treatment by printing an UV (ultraviolet ray)-setting type ink (reference numeral 12a designates a surface-treated layer) and semi-drying the ink, and then pressing both sheet members 11, 12 against each other.

The upper sheet member 11 can also be provided with a square through hole 13. In addition, the lower sheet member 12 can also have a square through hole 14, slightly smaller than the through hole 13, at an alignment position corresponding to the through hole 13. These through holes 13, 14 are provided at a position corresponding to the through hole 7 which passes through one internal electrode portion 6A formed in the substrate 1. Hole 15, which passes through both sheet members 11, 12 at the same time, is provided to correspond to the through hole 8 positioned in the vicinity of the other internal electrode portion 6B formed in the substrate 1. The upper surface of the upper sheet member 11 is subjected to a grafting process and an anchoring treatment by the use of a silane coupling agent and the like.

Reference numeral 16 designates a lower support layer formed on a lower surface side of the substrate 1. The lower support layer 16 is formed of a material, such as PET, having a sufficiently high electrical insulating property in the same manner as in the substrate 1 and the support layer 10 and is provided with a through hole 17 and a through hole 18 at a place corresponding to the other internal electrode portion 6B and the through hole 8, respectively, formed in the substrate 1. The lower support layer 16 is formed in the same manner as the support layer 10.

Reference numeral 19 designates a gelatinized internal solution charged in the through hole 14 of the lower sheet member 12. The gelatinized internal solution 19 is obtained by adding a gelatinizer (such as agar-agar, gelatine, glue, alginic acid, and various kinds of acrylic hygroscopic polymer) and a gel-evaporation inhibitor (such as glycerine and ethylene glycol) to a basic internal solution obtained by for example adding a phosphoric acid buffering solution to a 3.3 M-aqueous solution of KCl supersaturated with AgCl and formed in a disc-like shape.

The gelatinized internal solution 19 is charged by heating to turn it into a paste and then screen printing the resulting paste so that its upper surface may be slightly sunk below the upper surface of the upper sheet member 11. The gelatinized internal solution 19 is filled in the through hole 14 and connected to the internal electrode portion 6A through the electrically conductive portion 7a of the through hole 7 formed in the internal electrode portion 6A.

Reference numeral 20 designates an ion-selective response membrane adhesive paste being dropped onto the gelatinized internal solution 19. The ion-selective response membrane paste 20 is obtained, for example, in the following manner:

(1) PVC powders of 2.7 g and ortho-nitrophenyloctyl ether as a plasticizer of 5.4 g are put in an Erlenmeyer flask and tetrahydrofuran (hereinafter referred to as THF) as a solvent of 90 ml is added in the Erlenmeyer flask, drop by drop, to dissolve the PVC powders in THF. During this time period, it is desirable that the Erlenmeyer flask is lightly shaked to suitably disperse the PVC powders to completely dissolve them.

(2) Tri-octylphosphine oxide as a hydrogen ionresponse material of 0.135 g is dissolved in THF as a solvent of 10 ml to make a solution.

(3) The solution obtained in the above (1) is mixed with the solution obtained in the above (2) while thoroughly stirring them. During this time period, a part of the THF is evaporated (for about 15-30 minutes at room temperature) to obtain an ion-selective response membrane adhesive paste 20 having a predetermined viscosity.

The ion-selective response membrane paste 20 obtained in the above described manner is put in a syringe 21 and then upon dropping it in a predetermined quantity onto the gelatinized internal solution 19 drop by drop, as shown in FIG. 1, it adheres to an upper surface of the gelatinized internal solution 19 filled in the through hole 14 of the lower sheet member 12 and a part of the ion-selective response member paste 20 adheres to the sheet members 11, 12 forming the support layer 10 to generate a dissolving action between THF as a solvent contained in the ion-selective response membrane paste 20 and the sheet members 11, 12, thereby forming an ion-selective response membrane or film 22 having a predetermined film thickness e.g. in the range of 0.1 mm and also down to about 0.04 to 0.05 mm, due to the evaporation of the THF prior to its immediate diffusion and the membrane 22 solidifies so as to be integrated with the support layer 10, so that the ion-selective response membrane 22 is formed on the surface of the support layer 10 with a perfect seal against the support layer 10 to form a pH-measuring electrode P.

Reference numeral 23 designates a gel-immersed hydrophilic high molecular porous material filled in the through holes 15, 8 and 18 formed at a position corresponding to the support layer 10, the substrate 1 and the lower support layer 16, respectively. The gel-immersed hydrophilic high molecular porous material 23 is obtained by impregnating a hydrophilic high molecular porous material, which is obtained by sintering and molding a chemically stabilized hydrophilic high molecular particle, such as a sintered and molded body of an olefinic high polymer powder having a mechanical strength almost the same as that of polyolefine and a hydrophilicity given by the modifying treatment, [for example SUNFINE AQ (trade name) manufactured by Asahi Kasei Co., Ltd.], with a gelatinized composite, which does not deposit KCl after being left unattended in air and does not dry out, that is to say it does not lose the wetness characteristic of a surface of the porous material, such as a water-contained jelly mainly comprising a Na-salt of an acrylic polymer [for example U jelly (trade name) manufactured by Showa Denko Co., Ltd.]. The gel-immersed hydrophilic high molecular porous material 23 is filled in the through holes 15, 8 and 18 so as to slightly project over the surface of the support layer 10, and functions as a liquid junction portion of the reference electrode R.

Reference numeral 24 designates a gelatinized internal solution having the same chemical composition as the gelatinized internal solution 19 and adapted to be brought into contact with the internal electrode portion 6B through the through hole 17 formed in the lower support layer 16 and also into contact with the gel-immersed hydrophilic high molecular porous material 23. Reference numeral 25 designates a bottom case and reference numeral 26 designates a sample solution holder provided around the support layer 10.

In the formation of the above described sheet type composite electrode for use in the measurement of pH, a spreading action of the ion-selective response membrane paste 20 can be limited by using a fixed diluting magnification with THF in the formation of the ion-selective response membrane 22 as well as a fixed viscosity and quantity added drop by drop of the ion-selective response membrane paste 20. Thus, the ion-selective response membrane 22 having a fixed film thickness can be manufactured within several minutes, to permit a continuous production of a sheet type composite electrode.

Figure 4:
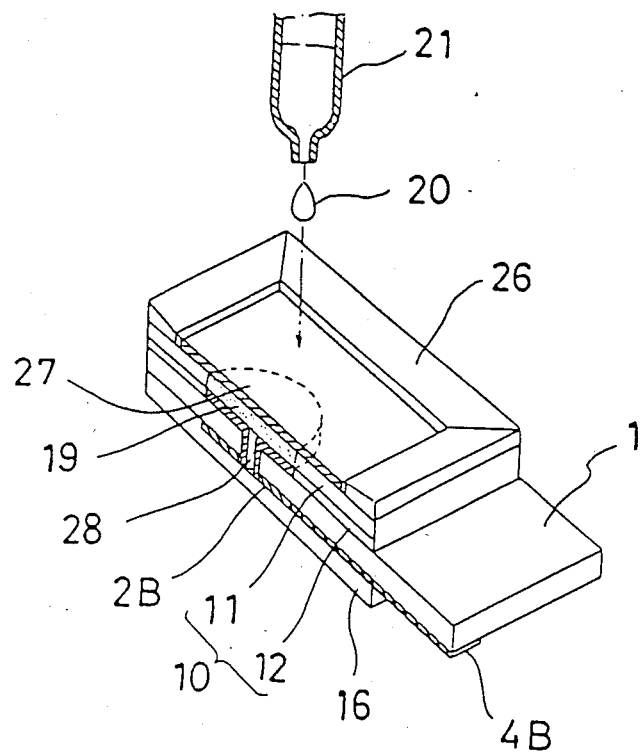
FIG. 4 is a partially broken perspective view showing another preferred embodiment of the present invention.
Figure 5:
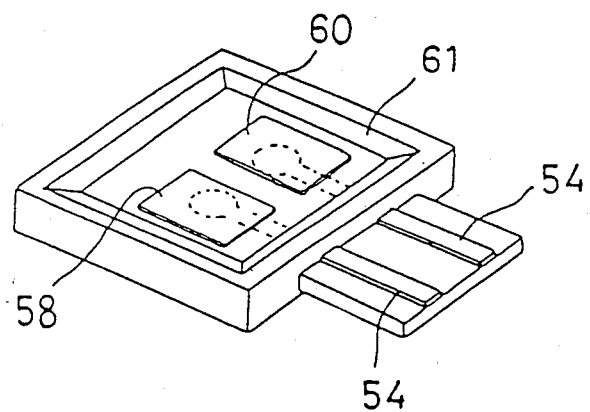
FIG. 5 and FIG. 6 are perspective views for describing the prior art, respectively.
Figure 6:
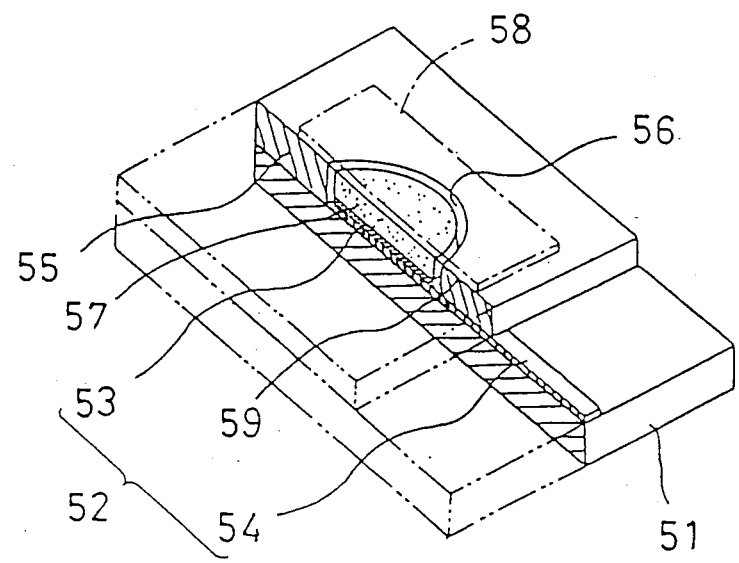

In addition, referring to FIG. 4, showing one example of an ion-response membrane electrode to which the present invention is applied, reference numeral 27 designates an ion-selective response membrane formed by solidifying the ion-selective response membrane paste 20. Reference numeral 28 designates a through hole electrode formed in the substrate 1 for connecting the gelatinized internal solution 19 to the lead electrode 2B.

Although the support layer 10 is formed of the sheet member 11 made of PET and the sheet member 12 made of PVC piled up, both the sheet members 11, 12 may be made of PVC.

Furthermore, the present invention is not limited to the above described preferred embodiments. For example, the present invention can be applied also to a PVC series liquid membrane type ion-selective electrode for measuring pNa, pK, pCl, pCa and the like.

According to the present invention, a support layer is formed of two sheet members having a sufficiently high electrical insulating property when piled up and a thin film-like ion-selective response membrane is formed by adding an ion-selective response membrane paste containing a solvent compatible with the support layer onto the support layer drop by drop, so that the response membrane can be formed within a short time with a perfect seal against the support layer. Accordingly, a sheet type electrode for use in the measurement of ions having a stabilized quality can be mass-produced.

What is claimed is:

1. In an electrode assembly for the measurement of ions, in which an ion-selective response membrane is formed on an upper surface of an insulating support layer, the improvement comprising;
   a pair of sheet members bound together to form the support layer, and
   means for providing the ion-selective response membrane on the support layer including an adhesive mixture-containing solvents that are compatible with a sealing adhesion to the support layer to form ion-selective response membrane.

2. The invention of claim 1 wherein the support layer is a laminate comprising a sheet material formed of polyethylene terephthalate and a sheet material formed of a polyvinyl chloride resin.

The invention of claim 1 further including a gelatinized internal solution mounted on the support layer beneath the ion-selective response membrane, the adhesive mixture is adhered directly on the gelatinized internal solution and the adjacent support layer to form the ion-selective response membrane when solidified.

3. The invention of claim 2 wherein the adjesive mixture includes a plasticizer, dissolved in tetrahydrofuran with tri-octylphosphine oxide.

4. The invention of claim 3 wherein polyvinyl chloride powder and ortho-nitrophenyl-octyl ether are mixed in a ration of 1:2 in tetrahydrofuran as a solvent until completely dissolved and tri-octylphosphine oxide is added to form the adhesive mixture.

5. The invention of claim 1 further including a gelatinized internal solution mounted on the support layer beneath the ion-selective response membrane, the adhesive mixture is adhered directly on the gelatinized internal solution and the adjacent support layer to form the ion-selective response membrane when solidified.

6. In an electrode assembly for the measurement of ions, in which an ion-selective response membrane is formed on an upper surface of an insulating support layer, the improvement comprising;
the support layer has an aperture, and a plastic film with a hydrogen ion-responsive material is formed integral with the support layer to extend across the aperture to form the outer surface of a pH measurement electrode assembly, the support layer being a laminate comprising a sheet material formed of polyethylene terephthalate and a sheet material formed of a polyvinyl chloride resin.

7. The invention of claim 6 further including a gelatinized internal solution mounted on the support layer beneath the ion-selective response membrane, the plastic film is adhered directly on the gelatinized internal solution and the adjacent support layer to form the ion-selective response membrane when solidified.

8. The invention of claim 6 wherein the plastic film is formed from an adhesive mixture including a plasticizer, dissolved in tetrahydrofuran with tri-octylphosphine oxide.

9. The invention of claim 8 wherein polyvinyl chloride powder and ortho-nitrophenyl-octyl ether are mixed in a ration of 1:2 in tetrahydrofuran as a solvent until completely dissolved and tri-octylphosphine oxide is added to form the adhesive mixture.

* * * * *